(12) United States Patent
Jin et al.

(10) Patent No.: US 10,151,704 B2
(45) Date of Patent: Dec. 11, 2018

(54) DEVICE FOR SINGLE MOLECULE DETECTION

(71) Applicants: Tsinghua University, Beijing (CN); HON HAI PRECISION INDUSTRY CO., LTD., New Taipei (TW)

(72) Inventors: Yuan-Hao Jin, Beijing (CN); Ying-Cheng Wang, Beijing (CN); Qun-Qing Li, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 18 days.

(21) Appl. No.: 15/636,581

(22) Filed: Jun. 28, 2017

(65) Prior Publication Data
US 2018/0136137 A1    May 17, 2018

(30) Foreign Application Priority Data
Nov. 14, 2016 (CN) .......................... 2016 1 1001903

(51) Int. Cl.
*G01J 3/44* (2006.01)
*G01N 21/65* (2006.01)
*B82Y 15/00* (2011.01)

(52) U.S. Cl.
CPC ............ *G01N 21/658* (2013.01); *B82Y 15/00* (2013.01); *Y10S 977/954* (2013.01)

(58) Field of Classification Search
CPC ........ G01J 3/02; G01J 3/44; G01N 2021/656; G01N 21/65; G01N 21/658
USPC .......................................................... 356/301
See application file for complete search history.

(56) References Cited

U.S. PATENT DOCUMENTS

| 4,259,682 | A | * | 3/1981 | Gamo | ..................... H01L 21/78 148/DIG. 28 |
|---|---|---|---|---|---|
| 8,805,536 | B2 | * | 8/2014 | Li | .......................... H01R 43/16 607/116 |
| 2005/0168745 | A1 | | 8/2005 | Naya | |
| 2007/0006625 | A1 | * | 1/2007 | Reinschke | .............. B21B 37/28 72/11.7 |
| 2011/0053794 | A1 | * | 3/2011 | Zhang | .................. B01J 19/0046 506/9 |

(Continued)

FOREIGN PATENT DOCUMENTS

| JP | 2005-195440 | 7/2005 |
|---|---|---|
| TW | 201307828 A | 2/2013 |

(Continued)

*Primary Examiner* — Md M Rahman
(74) *Attorney, Agent, or Firm* — ScienBiziP, P.C.

(57) ABSTRACT

The disclosure relates to a device for single molecule detection. The device includes a chamber having an inputting hole and an outputting hole, a carrier including a substrate and a metal layer located on the substrate, a detection device, and a controlling computer. The carrier includes a substrate and a metal layer on the substrate, wherein the substrate includes a base and a patterned bulge located on a surface of the base, the patterned bulge includes a number of strip-shaped bulges intersected with each other to form a net and define a number of holes, and the metal layer is located on the patterned bulge. The carrier for single molecule detection has a relative higher SERS and can enhance the Raman scattering.

20 Claims, 19 Drawing Sheets

(56) References Cited

U.S. PATENT DOCUMENTS

| | | | |
|---|---|---|---|
| 2011/0143466 A1* | 6/2011 | Chen | H01L 21/0242 438/29 |
| 2011/0238152 A1* | 9/2011 | Richter | A61F 2/915 623/1.15 |
| 2012/0170032 A1* | 7/2012 | Zhu | G01N 21/658 356/301 |
| 2012/0170033 A1* | 7/2012 | Zhu | G01N 21/658 356/301 |
| 2013/0038870 A1 | 2/2013 | Lin et al. | |
| 2013/0264307 A1* | 10/2013 | Lin | C01B 31/0438 216/49 |
| 2014/0074200 A1* | 3/2014 | Li | H01R 43/16 607/116 |
| 2015/0233832 A1* | 8/2015 | Maruyama | G01N 21/658 356/244 |
| 2015/0253596 A1* | 9/2015 | Zhang | G02F 1/1309 349/158 |
| 2016/0061993 A1* | 3/2016 | Ren | G02B 1/002 349/62 |
| 2016/0064612 A1* | 3/2016 | Ren | H01L 33/38 349/62 |
| 2016/0139511 A1* | 5/2016 | Li | H01J 37/32009 216/48 |
| 2016/0299047 A1* | 10/2016 | Molla | B01L 3/502784 |
| 2016/0329184 A1* | 11/2016 | Wei | H01J 1/14 |
| 2017/0123276 A1* | 5/2017 | Um | G02F 1/133345 |

FOREIGN PATENT DOCUMENTS

| | | |
|---|---|---|
| TW | I452282 A | 9/2014 |
| TW | 201619044 A | 6/2016 |

\* cited by examiner

DEVICE FOR SINGLE MOLECULE DETECTION

CROSS-REFERENCE TO RELATED APPLICATIONS

This application claims all benefits accruing under 35 U.S.C. § 119 from China Patent Application No. 201611001903.7, filed on Nov. 14, 2016, in the China Intellectual Property Office, the disclosure of which is incorporated herein by reference. This application is related to applications entitled, Ser. No. 15/633,770 "METHOD FOR MAKING CARRIER FOR SINGLE MOLECULE DETECTION", filed Jun. 27, 2017, Ser. No. 15/633,774 "CARRIER FOR SINGLE MOLECULE DETECTION", filed Jun. 27, 2017, and Ser. No. 15/633,775 "METHOD FOR DETECTING SINGLE MOLECULE", filed Jun. 27, 2017.

BACKGROUND

1. Technical Field

The present disclosure relates to a carrier for single molecule detection, a method for making the same, and a method for using the same to detect single molecules.

2. Description of Related Art

Raman spectroscopy is widely used for single molecule detection.

A method for detecting single molecules using Raman spectroscopy is provided. An aggregated silver particle film is coated on a surface of a glass substrate. A number of single molecule samples are disposed on the aggregated silver particle film. A laser irradiation is supplied to the single molecule samples by a Raman detection system to cause a Raman scattering and produce a Raman spectroscopy. The Raman spectroscopy is received by a sensor and analyzed by a computer. However, the surface of the glass substrate is usually smooth. Thus, the Raman scattering signal is not strong enough and the resolution of the single molecule is relatively low. Therefore, the glass substrate coated with aggregated silver particle film is not suitable for detecting low concentration single molecule samples.

What is needed, therefore, is a carrier for single molecule detection that overcomes the problems as discussed above.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
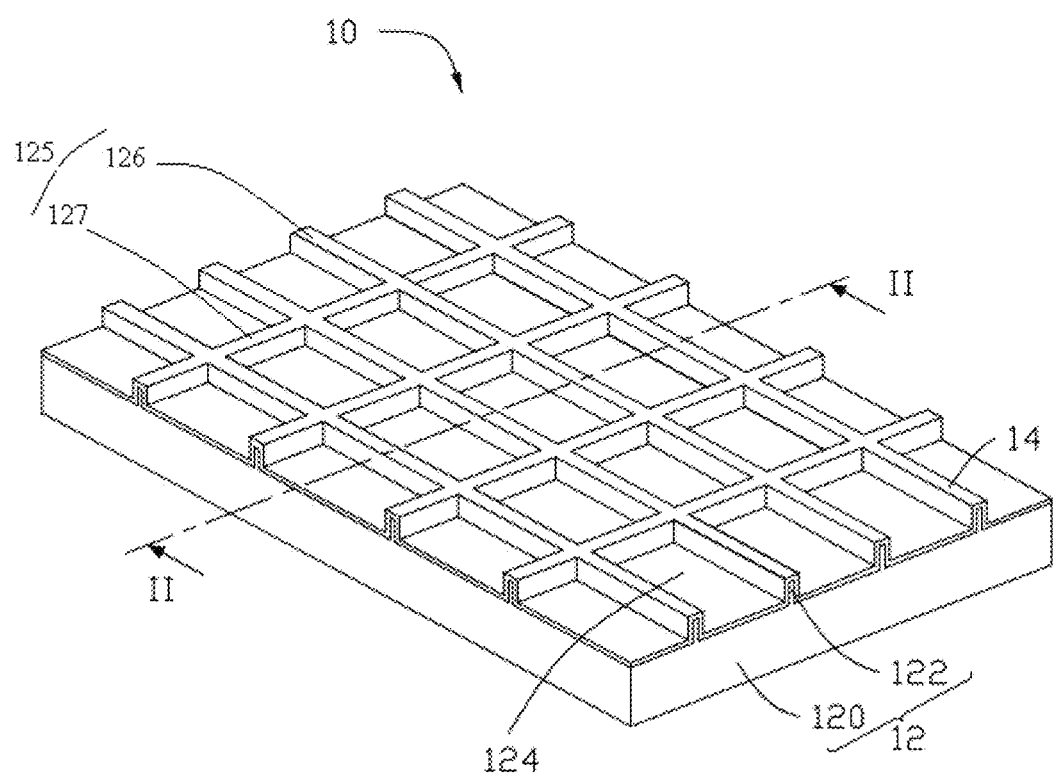
FIG. 1 is a schematic section view of one embodiment of a carrier for single molecule detection.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated better illustrate details and features. The description is not to considered as limiting the scope of the embodiments described herein.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

References will now be made to the drawings to describe, in detail, various embodiments of the present carrier for single molecule detection, a method for making the same, and a method for using the same to detect single molecules.

Figure 2:
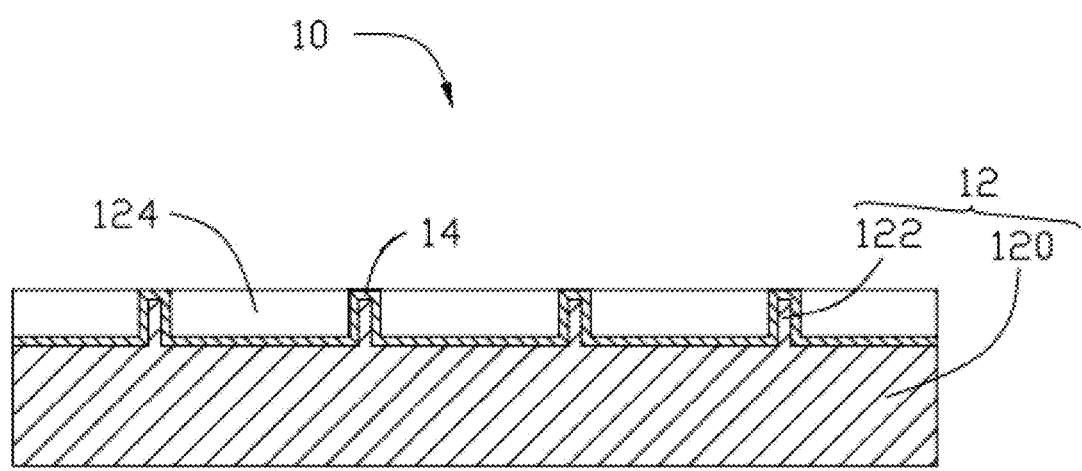
FIG. 2 is a cross-sectional view, along a line II-II of FIG. 1.
Figure 3:
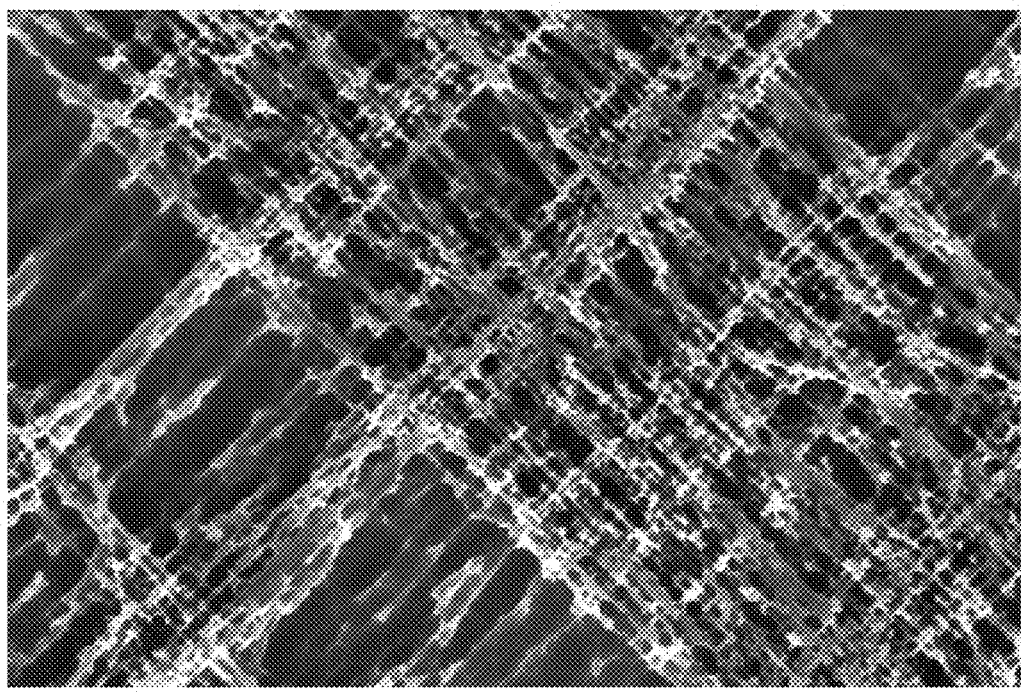
FIG. 3 is a Scanning Electron Microscope (SEM) image of a substrate of the carrier for single molecule detection of FIG. 1.
Figure 4:
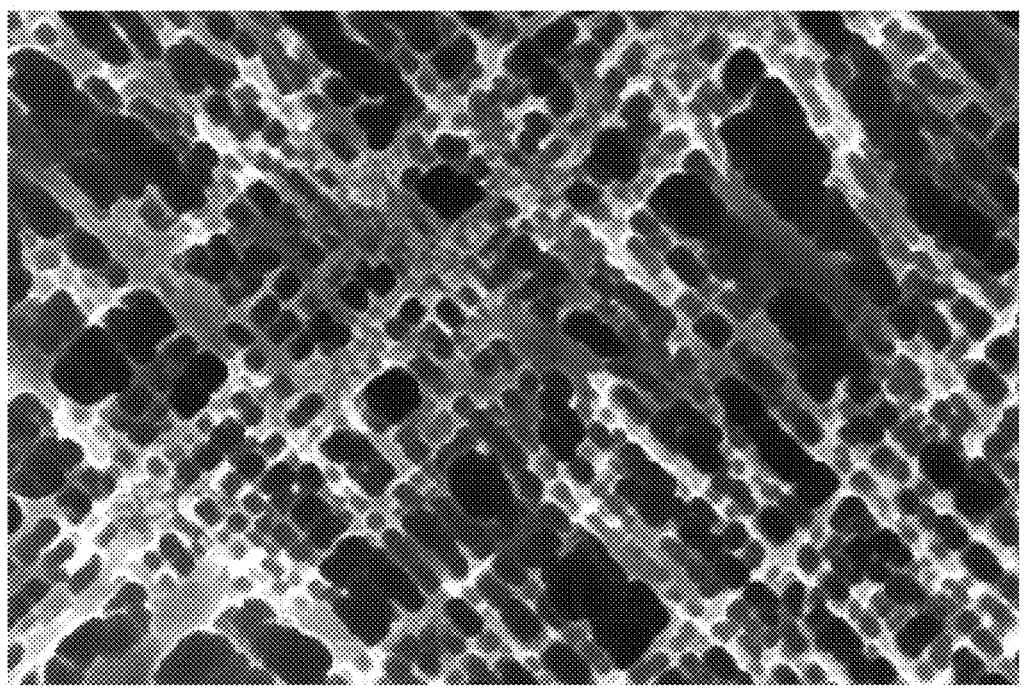
FIG. 4 is a partial enlarged image of the SEM image of FIG. 3.

Referring to FIGS. 1-2, a carrier 10 for single molecule detection of one embodiment is provided. The carrier 10 comprises a substrate 12 and a metal layer 14 located on the substrate 12. The substrate 12 comprises a base 120 and a patterned bulge 122 located on a surface of the base 120. The patterned bulge 122 comprises a plurality of strip-shaped bulges 125 intersected with each other to form a net and define a plurality of holes 124. In one embodiment, the plurality of strip-shaped bulges 125 is an intergrated structure as shown in FIGS. 3-4. The metal layer 14 is located on surfaces of the patterned bulge 122. The carrier 10 for single molecule detection has a relative higher SERS and can enhance the Raman scattering.

The substrate 12 can be an insulative substrate or a semiconductor substrate. The substrate 12 can be made of a material such as glass, quartz, silicon (Si), silicon dioxide ($SiO_2$), silicon nitride ($Si_3N_4$), gallium nitride (GaN), gallium arsenide (GaAs), alumina, or magnesia (MgO). The size and thickness of the substrate 12 can be selected according to need. In one embodiment, the substrate 12 is a silicon wafer.

The patterned bulge 122 and the base 120 can have the same material or different materials. In one embodiment, the patterned bulge 122 and the base 120 are an intergrated structure. The patterned bulge 122 can be located on a single surface or two opposite surfaces of the base 120. Each of the plurality of strip-shaped bulges 125 has a length less than or equal to the width of length of the base 120. The plurality of strip-shaped bulges 125 comprises a plurality of first strip-shaped bulges 126 and a plurality of second strip-shaped bulges 127. The plurality of first strip-shaped bulges 126 are substantially parallel with each other and extends along the first direction, and the plurality of second strip-shaped bulges 127 are substantially parallel with each other and extends along the second direction different from the first direction. The angle between the first direction and the second direction is greater than 0 degrees an less than or equal to 90 degrees. In one embodiment, the angle between the first direction and the second direction is greater than 30 degrees.

The width of the plurality of strip-shaped bulges 125 can be in a range from about 20 nanometers to about 150 nanometers. In one embodiment, the width of the plurality of strip-shaped bulges 125 can be in a range from about 20 nanometers to about 100 nanometers. In one embodiment, the width of the plurality of strip-shaped bulges 125 can be in a range from about 20 nanometers to about 50 nanometers. The distance between adjacent two of the plurality of strip-shaped bulges 125 can be in a range from about 10 nanometers to about 300 nanometers. In one embodiment, the distance between adjacent two of the plurality of strip-shaped bulges 125 can be in a range from about 10 nanometers to about 100 nanometers. In one embodiment, the distance between adjacent two of the plurality of strip-shaped bulges 125 can be in a range from about 10 nanometers to about 50 nanometers. The height of the plurality of strip-shaped bulges 125 can be in a range from about 50 nanometers to about 1000 nanometers. In one embodiment, the height of the plurality of strip-shaped bulges 125 can be in a range from about 500 nanometers to about 1000 nanometers. The average diameter of the plurality of holes 124 can be in a range from about 10 nanometers to about 300 nanometers, and the depth of the plurality of holes 124 can be in a range from about 50 nanometers to about 1000 nanometers. In one embodiment, the ratio between the depth and the average diameter is greater than 5. In one embodiment, the ratio between the depth and the average diameter is greater than 10.

The metal layer 14 can be located on both top and side surfaces of the plurality of strip-shaped bulges 125 and bottom surfaces of the plurality of holes 124. The metal layer 14 can be a continuous structure and covers the entire surface of the substrate 12. The metal layer 14 can also be a discontinuous structure. The metal layer 14 can be a single-layer or a multi-layer structure. The thickness of the metal layer 14 can be in a range from about 2 nanometers to about 200 nanometers. The material of the metal layer 14 can be gold, silver, copper, iron, nickel, aluminum, or any alloy thereof. The metal layer 14 can be uniformly deposited on the surface of the substrate 12 by a method of electron beam evaporation, chemical vapor deposition (CVD), or sputtering. In one embodiment, the metal layer 14 is a gold layer with a thickness of about 20 nanometers.

Figure 5:
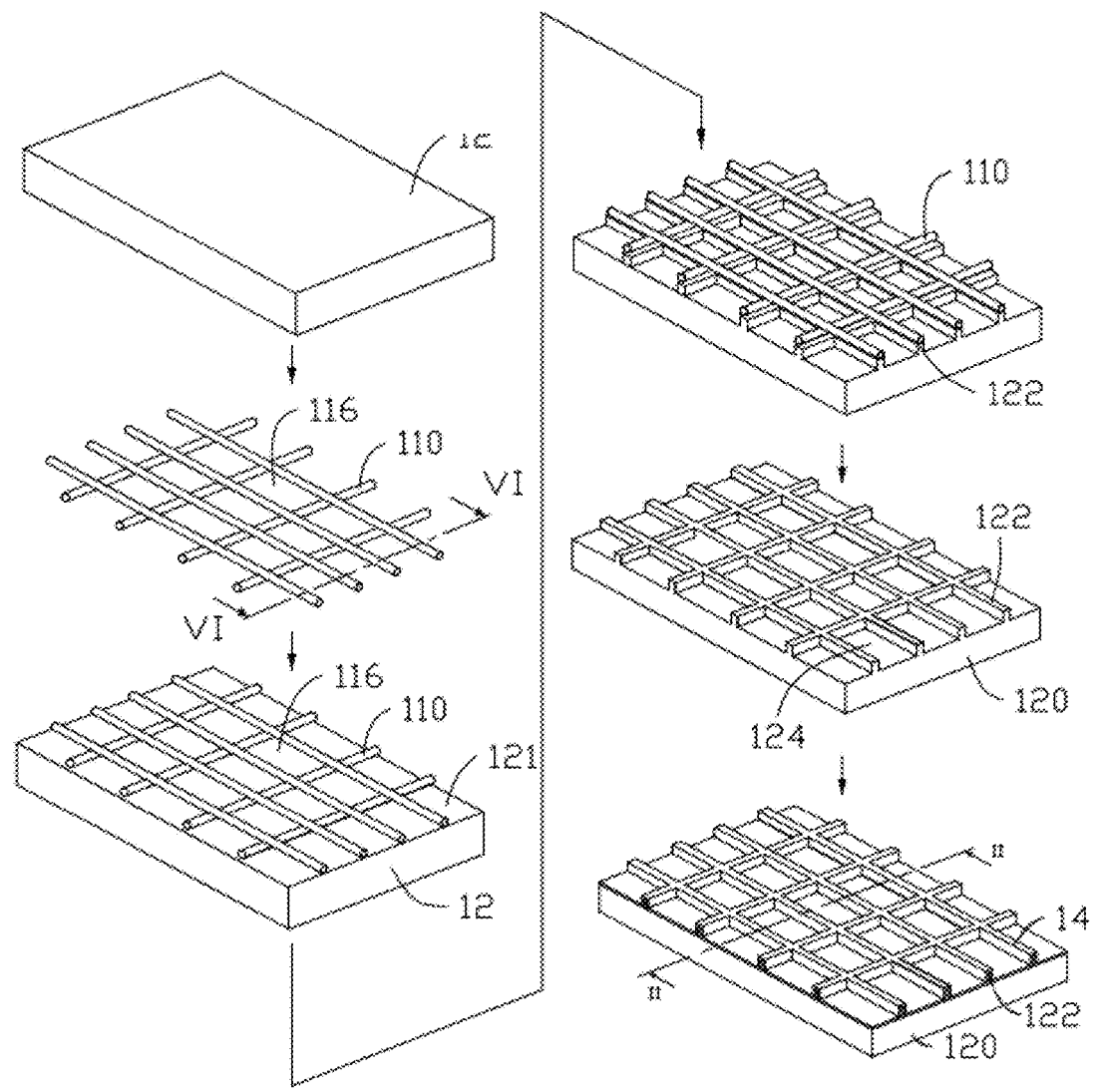
FIG. 5 is a flowchart of one embodiment of a method for making the carrier for single molecule detection of FIG. 1.
Figure 6:
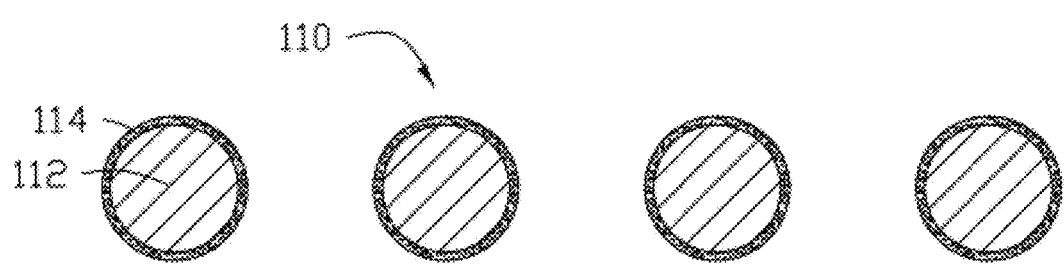
FIG. 6 is a cross-sectional view along line VI-VI of a carbon nanotube composite structure of FIG. 5.

Referring to FIGS. 5-6, a method for making the carrier 10 of one embodiment includes the following steps:

step (S10), providing the substrate 12;

step (S20), providing a carbon nanotube composite structure 110, wherein the carbon nanotube composite structure 110 includes a plurality of intersected carbon nanotubes and defines a plurality of openings 116;

step (S30), placing the carbon nanotube composite structure 110 on a surface 121 of the substrate 12, wherein parts of the surface 121 are exposed from the plurality of openings 116;

step (S40), forming the patterned bulge 122 on the surface 121 by dry etching the surface 121 using the carbon nanotube composite structure 110 as a first mask, wherein the patterned bulge 122 includes a plurality of strip-shaped bulges 125 intersected with each other;

step (S50), removing the carbon nanotube composite structure 110; and step (S60), applying a metal layer 14 on the patterned bulge 122.

In step (S10), the material of the substrate 12 is not limited and can be metal, insulating material or semiconductor. The metal can be gold, aluminum, nickel, chromium, or copper. The insulating material can be silicon dioxide or silicon nitride. The semiconductor can be silicon, gallium nitride, or gallium arsenide. In one embodiment, the material of the substrate 12 is a gallium nitride layer with a thickness of 300 micrometers.

In step (S20), the carbon nanotube composite structure 110 includes a carbon nanotube structure 112 and a protective layer 114 coated on the carbon nanotube structure 112 as shown in FIG. 6. The carbon nanotube structure 112 is a free-standing structure. The term "free-standing structure" includes that the carbon nanotube structure 112 can sustain the weight of itself when it is hoisted by a portion thereof without any significant damage to its structural integrity. Thus, the carbon nanotube structure 112 can be suspended by two spaced supports.

The plurality of carbon nanotubes can be single-walled carbon nanotubes, double-walled carbon nanotubes, or multi-walled carbon nanotubes. The length and diameter of the plurality of carbon nanotubes can be selected according to need. The diameter of the single-walled carbon nanotubes can be in a range from about 0.5 nanometers to about 10 nanometers. The diameter of the double-walled carbon nanotubes can be in a range from about 1.0 nanometer to about 15 nanometers. The diameter of the multi-walled carbon nanotubes can be in a range from about 1.5 nanometers to about 50 nanometers. In one embodiment, the length of the carbon nanotubes can be in a range from about 200 micrometers to about 900 micrometers.

The plurality of carbon nanotubes are orderly arranged to form an ordered carbon nanotube structure. The plurality of carbon nanotubes extend along a direction substantially parallel to the surface of the carbon nanotube structure 112. The term 'ordered carbon nanotube structure' includes, but is not limited to, a structure wherein the plurality of carbon nanotubes are arranged in a consistently systematic manner, e.g., the plurality of carbon nanotubes are arranged approximately along the same direction.

The carbon nanotube structure 112 defines a plurality of apertures. The aperture extends throughout the carbon nanotube structure 112 along the thickness direction thereof. The aperture can be a hole defined by several adjacent carbon nanotubes, or a gap defined by two substantially parallel carbon nanotubes and extending along axial direction of the carbon nanotubes. The hole shaped aperture and the gap shaped aperture can exist in the carbon nanotube structure 112 at the same time. Hereafter, the size of the aperture is the diameter of the hole or width of the gap. The sizes of the apertures can be different. The average size of the apertures can be in a range from about 10 nanometers to about 500 micrometers. For example, the sizes of the apertures can be about 50 nanometers, 100 nanometers, 500 nanometers, 1 micrometer, 10 micrometers, 80 micrometers, or 120 micrometers.

The carbon nanotube structure 112 can include at least one carbon nanotube film, at least one carbon nanotube wire, or combination thereof. In one embodiment, the carbon nanotube structure 112 can include a single carbon nanotube film or two or more carbon nanotube films stacked together. Thus, the thickness of the carbon nanotube structure 112 can be controlled by the number of the stacked carbon nanotube films. The number of the stacked carbon nanotube films can be in a range from about 2 to about 100. For example, the number of the stacked carbon nanotube films can be 10, 30, or 50. In one embodiment, the carbon nanotube structure 112 is formed by folding a single carbon nanotube wire. In one embodiment, the carbon nanotube structure 112 can include a layer of parallel and spaced carbon nanotube wires. Also, the carbon nanotube structure 112 can include a plurality of carbon nanotube wires intersected or weaved together to form a carbon nanotube net. The distance between two adjacent parallel and spaced carbon nanotube wires can be in a range from about 0.1 micrometers to about 200 micrometers. In one embodiment, the distance between two adjacent parallel and spaced carbon nanotube wires is in a range from about 10 micrometers to about 100 micrometers. The gap between two adjacent substantially parallel carbon nanotube wires is defined as the apertures. The size of the apertures can be controlled by controlling the distance between two adjacent parallel and spaced carbon nanotube wires. The length of the gap between two adjacent parallel carbon nanotube wires can be equal to the length of the carbon nanotube wire. It is understood that any carbon nanotube structure described can be used with all embodiments.

Figure 7:
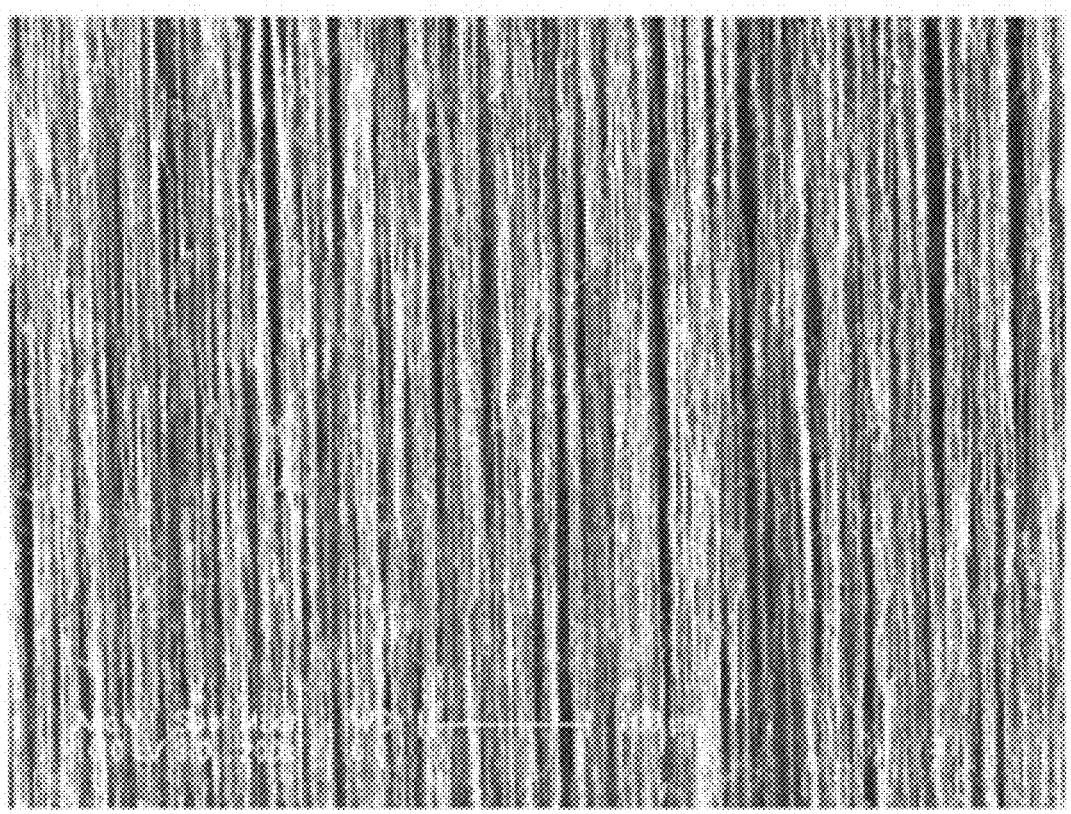
FIG. 7 is an SEM image of a drawn carbon nanotube film of one embodiment.

In one embodiment, the carbon nanotube structure 112 includes at least one drawn carbon nanotube film. The drawn carbon nanotube film can be drawn from a carbon nanotube array that is able to have a film drawn therefrom. The drawn carbon nanotube film includes a plurality of successive and oriented carbon nanotubes joined end-to-end by van der Waals attractive force therebetween. The drawn carbon nanotube film is a free-standing film. Referring to FIG. 7, each drawn carbon nanotube film includes a plurality of successively oriented carbon nanotube segments joined end-to-end by van der Waals attractive force therebetween. Each carbon nanotube segment includes a plurality of carbon nanotubes parallel to each other, and combined by van der Waals attractive force therebetween. As can be seen in FIG. 7, some variations can occur in the drawn carbon nanotube film. The carbon nanotubes in the drawn carbon nanotube film are oriented along a preferred orientation. The drawn carbon nanotube film can be treated with an organic solvent to increase the mechanical strength and toughness and reduce the coefficient of friction of the drawn carbon nanotube film. A thickness of the drawn carbon nanotube film can range from about 0.5 nanometers to about 100 micrometers. The drawn carbon nanotube film defines a plurality of apertures between adjacent carbon nanotubes.

The carbon nanotube structure 112 can include at least two stacked drawn carbon nanotube films. In other embodiments, the carbon nanotube structure 112 can include two or more coplanar carbon nanotube films, and can include layers of coplanar carbon nanotube films. Additionally, when the carbon nanotubes in the carbon nanotube film are aligned along one preferred orientation (e.g., the drawn carbon nanotube film), an angle can exist between the orientation of carbon nanotubes in adjacent films, whether stacked or adjacent. Adjacent carbon nanotube films can be combined by only the van der Waals attractive force therebetween. An angle between the aligned directions of the carbon nanotubes in two adjacent carbon nanotube films can range from about 0 degrees to about 90 degrees. When the angle between the aligned directions of the carbon nanotubes in adjacent stacked drawn carbon nanotube films is larger than 0 degrees, a plurality of micropores is defined by the carbon nanotube structure 112. In one embodiment, the carbon nanotube structure 112 has the aligned directions of the carbon nanotubes between adjacent stacked drawn carbon nanotube films at 90 degrees. Stacking the carbon nanotube films will also add to the structural integrity of the carbon nanotube structure 112.

Figure 8:
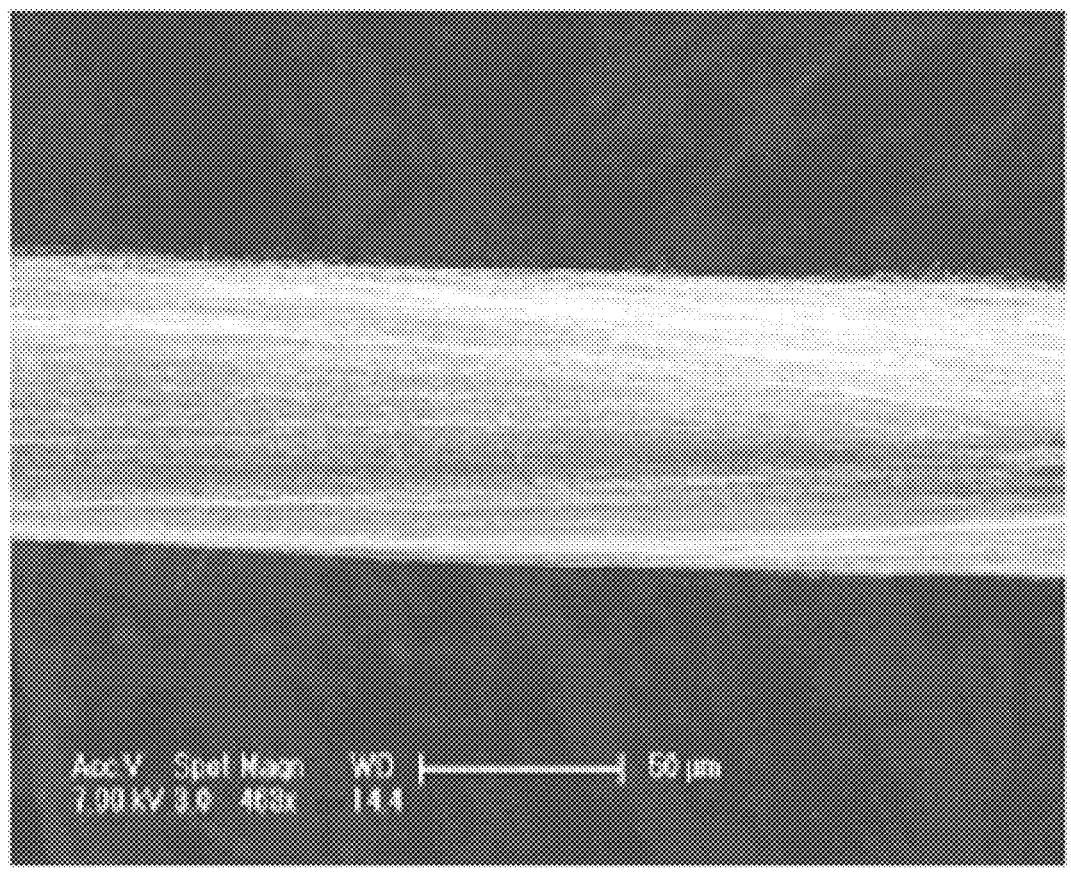
FIG. 8 is an SEM image of an untwisted carbon nanotube wire of one embodiment.

The carbon nanotube wire can be untwisted or twisted. Treating the drawn carbon nanotube film with a volatile organic solvent can form the untwisted carbon nanotube wire. Specifically, the organic solvent is applied to soak the entire surface of the drawn carbon nanotube film. During the soaking, adjacent parallel carbon nanotubes in the drawn carbon nanotube film will bundle together, due to the surface tension of the organic solvent as it volatilizes, and thus, the drawn carbon nanotube film will be shrunk into an untwisted carbon nanotube wire. Referring to FIG. 8, the untwisted carbon nanotube wire includes a plurality of carbon nanotubes substantially oriented along the same direction (i.e., a direction along the length of the untwisted carbon nanotube wire). The carbon nanotubes are substantially parallel to the axis of the untwisted carbon nanotube wire. More specifically, the untwisted carbon nanotube wire includes a plurality of successive carbon nanotube segments joined end to end by van der Waals attractive force therebetween. Each carbon nanotube segment includes a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire ranges from about 0.5 nanometers to about 100 micrometers.

Figure 9:
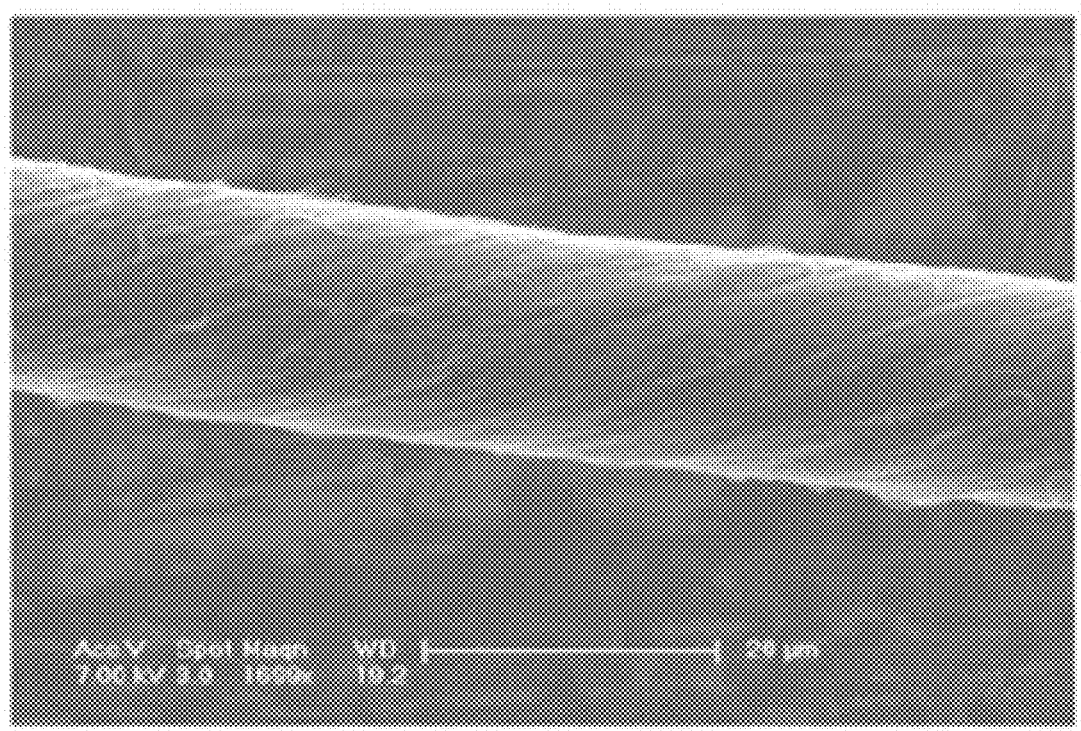
FIG. 9 is an SEM image of a twisted carbon nanotube wire of one embodiment.

The twisted carbon nanotube wire can be formed by twisting a drawn carbon nanotube film using a mechanical force to turn the two ends of the drawn carbon nanotube film in opposite directions. Referring to FIG. 9, the twisted carbon nanotube wire includes a plurality of carbon nanotubes helically oriented around an axial direction of the twisted carbon nanotube wire. More specifically, the twisted carbon nanotube wire includes a plurality of successive carbon nanotube segments joined end to end by van der Waals attractive force therebetween. Each carbon nanotube segment includes a plurality of carbon nanotubes parallel to each other, and combined by van der Waals attractive force therebetween. The length of the carbon nanotube wire can be set as desired. A diameter of the twisted carbon nanotube wire can be from about 0.5 nanometers to about 100 micrometers. Further, the twisted carbon nanotube wire can be treated with a volatile organic solvent after being twisted to bundle the adjacent paralleled carbon nanotubes together. The specific surface area of the twisted carbon nanotube wire will decrease, while the density and strength of the twisted carbon nanotube wire will increase.

The carbon nanotube composite structure 110 can be made by applying a protective layer 114 on a surface of the carbon nanotube structure 112. The carbon nanotube structure 112 can be suspended in a depositing chamber during depositing the protective layer 114 so that two opposite surfaces of the carbon nanotube structure 112 are coated with the protective layer 114. In some embodiments, each of the plurality of carbon nanotubes is fully enclosed by the protective layer 114. In one embodiment, the carbon nanotube structure 112 is located on a frame so that the middle portion of the carbon nanotube structure 112 is suspended through the through hole of the frame. The frame can be any shape, such as a quadrilateral. The carbon nanotube structure 112 can also be suspended by a metal mesh or metal ring.

The method of depositing the protective layer 114 can be physical vapor deposition (PVD), chemical vapor deposition (CVD), atomic layer deposition (ALD), magnetron sputtering, or spraying.

The plurality of openings 116 are formed because of the plurality of apertures of the carbon nanotube structure 112. The plurality of openings 116 and the plurality of apertures have the same shape and different size. The size of the plurality of openings 116 is smaller than that of the plurality of apertures because the protective layer 114 is deposited in the plurality of apertures.

The thickness of the protective layer 114 is in a range from about 3 nanometers to about 50 nanometers. In one embodiment, the thickness of the protective layer 114 is in a range from about 3 nanometers to about 20 nanometers. If the thickness of the protective layer 114 is less than 3 nanometers, the protective layer 114 cannot prevent the carbon nanotubes from being destroyed in following etching process. If the thickness of the protective layer 114 is greater than 50 nanometers, the plurality of apertures may be fully filled by the protective layer 114 and the plurality of openings 116 cannot be obtained.

The material of the protective layer 114 can be metal, metal oxide, metal nitride, metal carbide, metal sulfide, silicon oxide, silicon nitride, or silicon carbide. The metal can be gold, nickel, titanium, iron, aluminum, titanium, chromium, or alloy thereof. The metal oxide can be alumina, magnesium oxide, zinc oxide, or hafnium oxide. The material of the protective layer 114 is not limited above and can be any material as long as the material can be deposited on the carbon nanotube structure 112, would not react with the carbon nanotubes and would not be etched easily in following drying etching process. The protective layer 114 is combined with the carbon nanotube structure 112 by van der Waals attractive force therebetween only.

Figure 10:
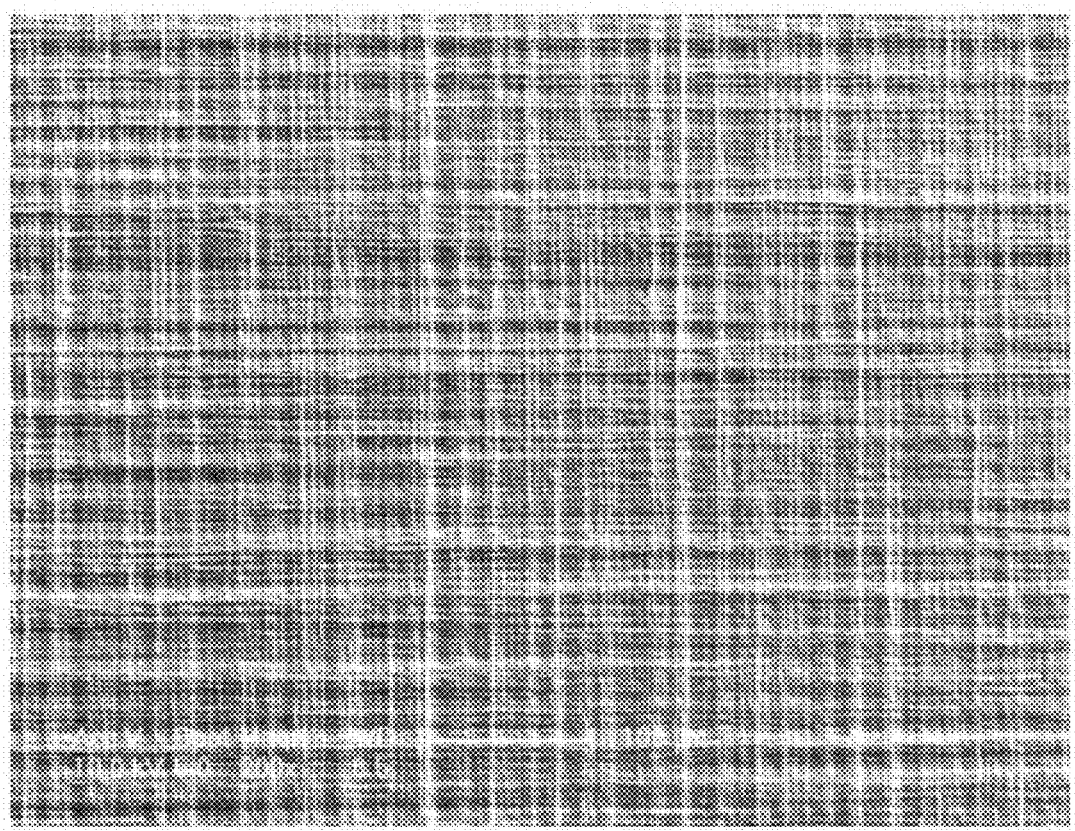
FIG. 10 is an SEM image of a carbon nanotube composite structure of one embodiment.
Figure 11:
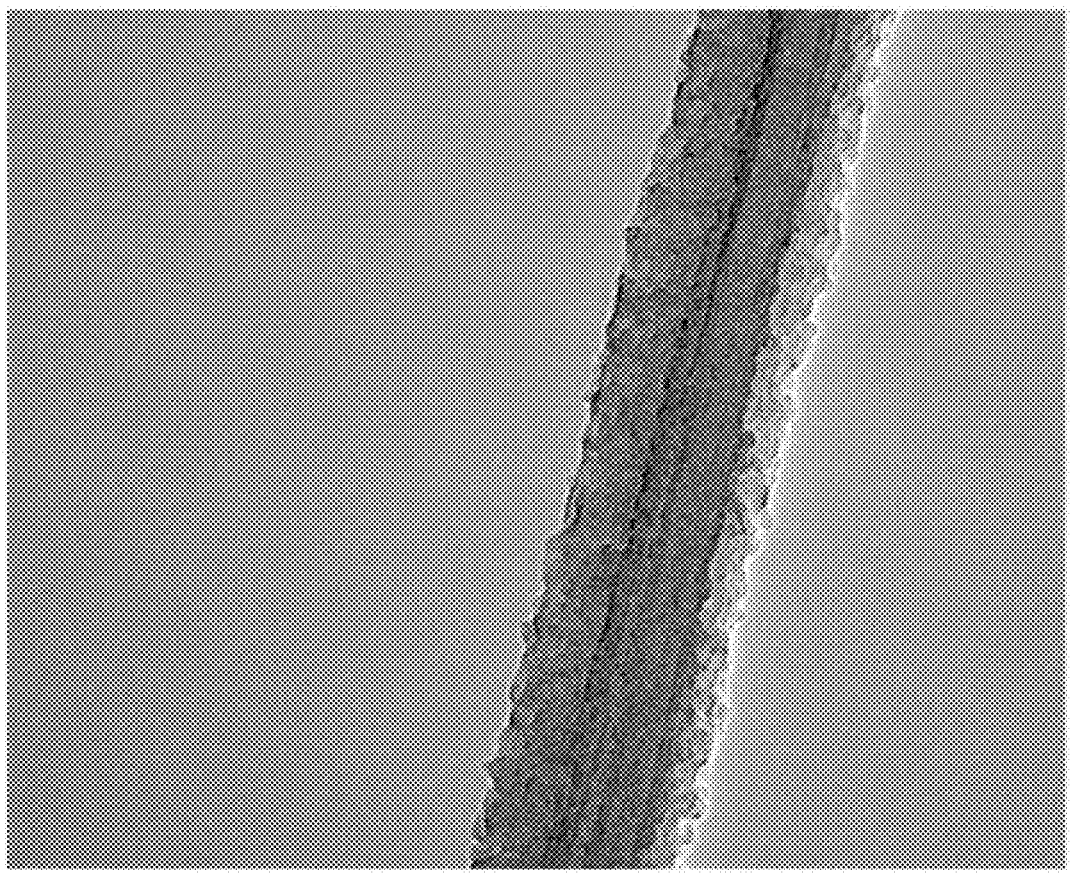
FIG. 11 is an SEM image of a single carbon nanotube coated with an alumina ($Al_2O_3$) layer.

As shown in FIG. 10, in one embodiment, an alumina layer of 5 nanometers thickness is deposited on two stacked drawn carbon nanotube films by electron beam evaporation. As shown in FIG. 11, each of the carbon nanotubes is entirely coated by the alumina layer. The aligned direction of the carbon nanotubes between adjacent stacked drawn carbon nanotube films is 90 degrees.

In step (S30), the carbon nanotube composite structure 110 can be in direct contact with the surface 121 of the substrate 12 or suspended above the surface 121 of the substrate 12 by a support. In one embodiment, the carbon nanotube composite structure 110 is transferred on the surface 121 of the substrate 12 through the frame.

In one embodiment, the placing the carbon nanotube composite structure 110 on the surface 121 further comprises solvent treating the substrate 12 with the carbon nanotube composite structure 110 thereon. Because there is air between the carbon nanotube composite structure 110 and the surface 121 of the substrate 12, the solvent treating can exhaust the air and allow the carbon nanotube composite structure 110 to be closely and firmly adhered on the surface 121 of the substrate 12. The solvent treating can be applying a solvent to entire surface of the carbon nanotube composite structure 110 or immersing the entire substrate 12 with the carbon nanotube composite structure 110 in a solvent. The solvent can be water or volatile organic solvent such as ethanol, methanol, acetone, dichloroethane, chloroform, or mixtures thereof. In one embodiment, the organic solvent is ethanol.

In the step (S40), the dry etching can be plasma etching or reactive ion etching (RIE). In one embodiment, the dry etching is performed by applying plasma energy on the entire or part surface of the surface 121 via a plasma device. The plasma gas can be an inert gas and/or etching gases, such as argon (Ar), helium (He), chlorine ($Cl_2$), hydrogen ($H_2$), oxygen ($O_2$), fluorocarbon ($CF_4$), ammonia ($NH_3$), or air.

In one embodiment, the plasma gas is a mixture of chlorine and argon. The power of the plasma device can be in a range from about 20 watts to about 70 watts. The plasma flow of chlorine can be in a range from about 5 sccm to about 20 sccm, such as 10 sccm. The plasma flow of argon can be in a range from about 15 sccm to about 40 sccm, such as 25 sccm. When the plasma is produced in vacuum, the work pressure of the plasma can be in a range from about 3 Pa to 10 Pa, such as 6 Pa. The time for plasma etching can be in a range from about 10 seconds to about 20 seconds, such as 15 seconds.

In the plasma etching process, the plasma gas would react with the exposed portion of the substrate 12 and would not react with the protective layer 114, or reaction between the plasma gas and the protective layer 114 is much slower than reaction between the plasma gas and the substrate 12. The selection relationship of the plasma gas, material of the substrate 12 and material of the protective layer 114 is shown in Table 1 below.

TABLE 1

| Number | Substrate | protective layer | Plasma gas |
|---|---|---|---|
| 1 | Al | $SiO_2$ | $Cl_2$ or $BCl_3$ |
| 2 | $SiO_2$ | Al, Cr, Fe, Ti, Ni, or Au | $CF_4$ |
| 3 | $SiN_x$ | Al, Cr, Fe, Ti, Ni, or Au | $CF_4$ |
| 4 | GaN | $Al_2O_3$ | $Cl_2$ or $Ar_2$ |
| 5 | Au, Cr or Ni | $SiO_2$ or $SiN_x$ | $O_2$ or $Ar_2$ |
| 6 | Cu | $SiO_2$ or $SiN_x$ | $O_2$ or $BCl_3$ |

In the etching process, the etching gas reacts with the substrate 12, but does not react with the protective layer 114 or react with the protective layer 114 at a speed much less than that of the reaction between the etching gas and the substrate 12. Thus, the exposed portion of the substrate 12 would be etched gradually and the portion of the substrate 12 that are shielded by the carbon nanotube composite structure 110 would not be etched.

The patterned bulge 122 and the carbon nanotube composite structure 110 substantially have the same pattern. When the carbon nanotube structure 112 includes a plurality of intersected drawn carbon nanotube films, the patterned bulge 122 includes a plurality of strip-shaped bulges 125 intersected with each other to form a net structure as shown in FIG. 3.

The plurality of strip-shaped bulges 125 can have a width in a range from about 20 nanometers to about 150 nanometers, a distance in a range from about 10 nanometers to about 300 nanometers, and a height in a range from about 50 nanometers to about 1000 nanometers.

After coating with the protective layer 114, the diameter of the carbon nanotubes are about tens of nanometers, and distance between adjacent two carbon nanotubes are about tens of nanometers. Thus, the width and distance of the plurality of strip-shaped bulges 125 are also tens of nanometers, and the average diameter of the plurality of hole 124 are also tens of nanometers. The density of the strip-shaped bulges 125 and the hole 124 would be increased. For example, when both the width and distance of the plurality of strip-shaped bulges 125 are 20 nanometers, the number of the strip-shaped bulges 125 and the hole 124 would be 50 within 1 micrometer. The conventional photolithography method cannot make all the strip-shaped bulges in nanoscale and obtain this density due to the resolution limitation. At the gap between two adjacent the plurality of strip-shaped bulges 125, a surface plasmon resonance (SPR) is produced on a surface of the metal layer 14 so that the surface-enhanced Raman scattering (SERS) of the carrier 10 will be outstandingly enhanced. The enhancement factor of SERS of the carrier 10 can be in a range from about $10^5$ to about $10^{15}$. In one embodiment, the enhancement factor of SERS of the carrier 10 is about $10^{10}$.

In step (S50), the method of removing the carbon nanotube composite structure 110 can be ultrasonic method, or adhesive tape peeling, oxidation. In one embodiment, the substrate 12 with the carbon nanotube composite structure 110 thereon is placed in an N-methyl pyrrolidone solution and ultrasonic treating for several minutes.

Figure 12:
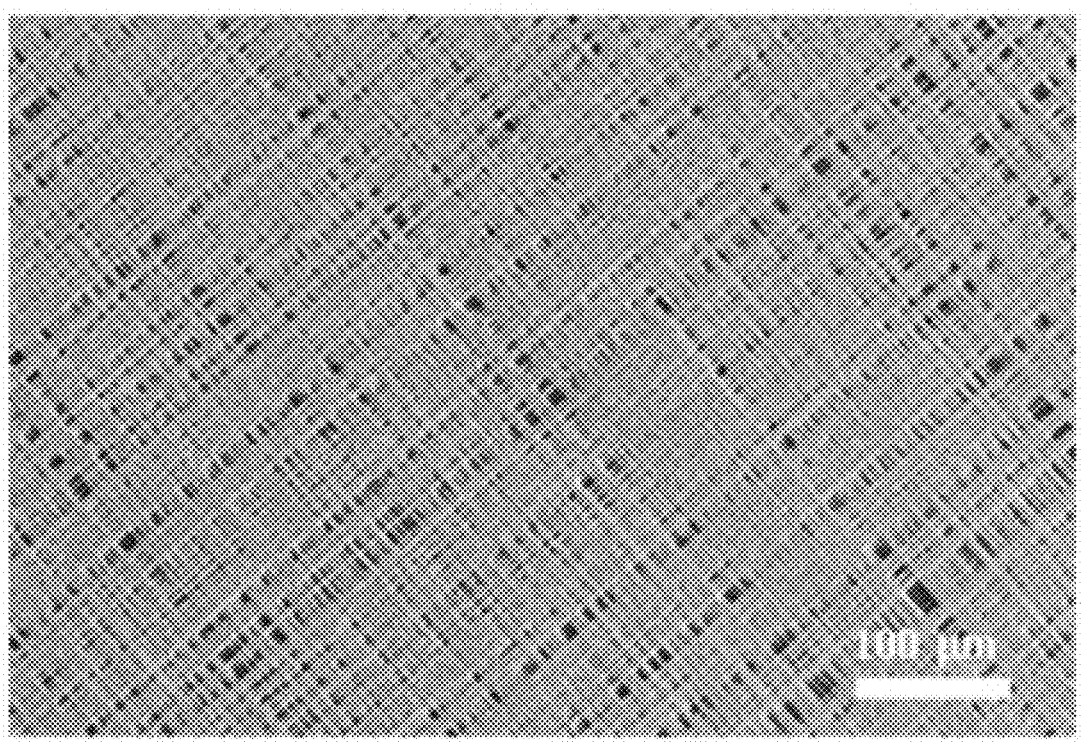
FIG. 12 is a top view SEM image of the carrier for single molecule detection made by the method of FIG. 5.
Figure 13:
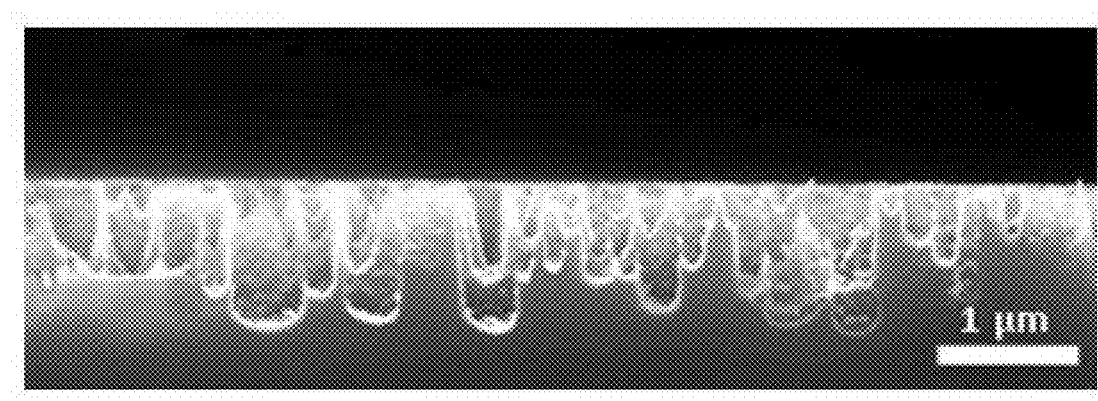
FIG. 13 is a cross-sectional view SEM image of the carrier for single molecule detection made by the method of FIG. 5.

In step (S60), the metal layer 14 can be deposited on the patterned bulge 122 by a method of electron beam evaporation, ion beam sputtering, atomic layer deposition, magnetron sputtering, thermal vapor deposition, or chemical vapor deposition. The thickness of the metal layer 14 can be in a range from about 2 nanometers to about 200 nanometers. The material of the metal layer 14 can be gold, silver, copper, iron, nickel, aluminum or alloy thereof. In one embodiment, the metal layer 14 is a gold layer with a thickness of about 20 nanometers. As shown in FIG. 12, the gold layer covers entire surfaces of the patterned bulge 122. As shown in FIG. 13, the gold layer is in direct contact with the bottom surfaces of the hole.

Figure 14:
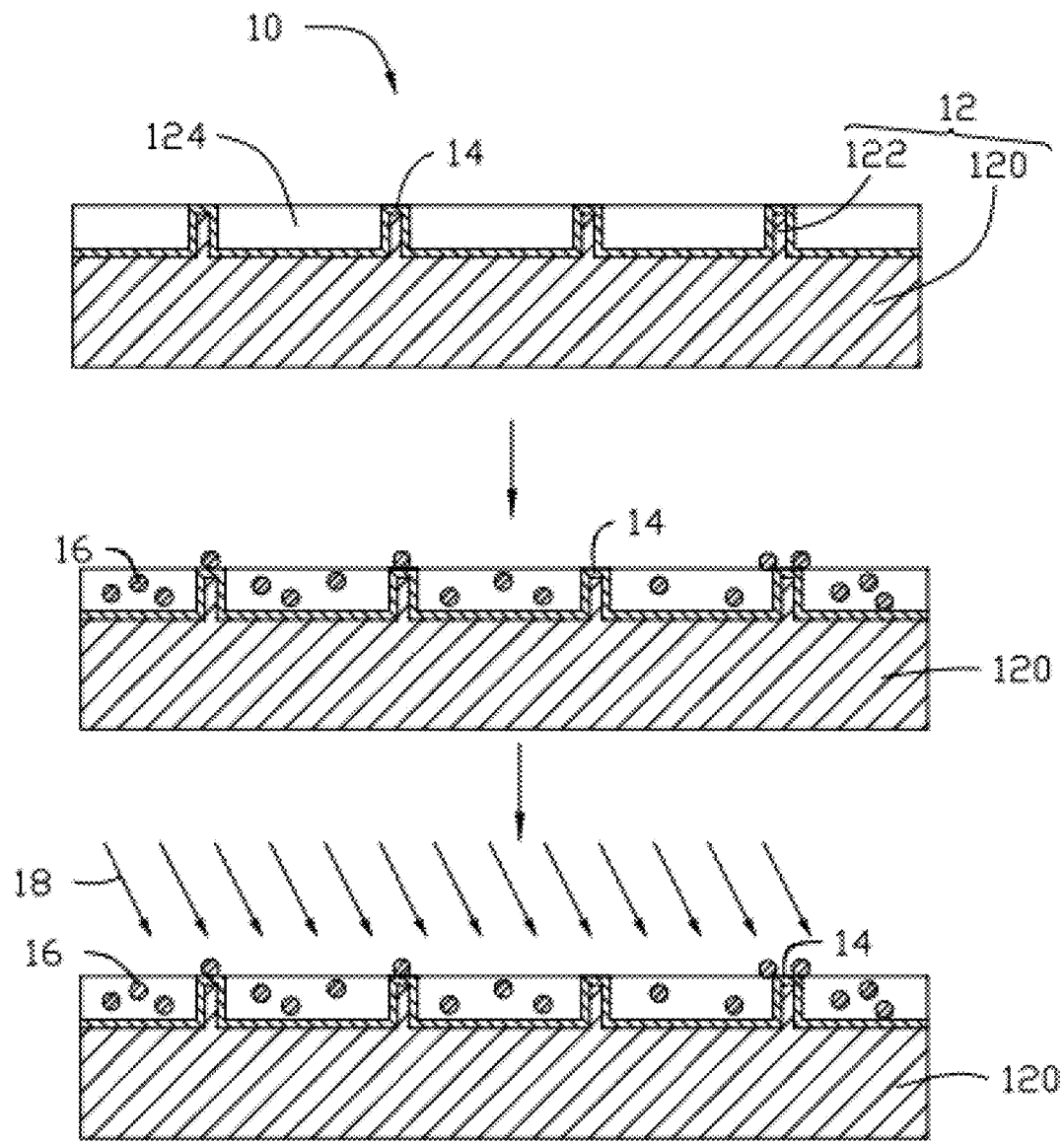
FIG. 14 is a flowchart of one embodiment of a method for detecting single molecules.

Referring to FIG. 14, a method for detecting single molecule of one embodiment includes the following steps:

step (S11), providing the carrier 10, wherein the carrier 100 comprising a substrate 12 and a metal layer 14 located on the substrate 12, the substrate 12 comprises a base 120 and a patterned bulge 122 located on a surface of the base 120, the patterned bulge 122 comprises a plurality of strip-shaped bulges 125 intersected with each other to form a net and define a number of holes 124, and the metal layer 14 is located on the patterned bulge 122;

step (S12), disposing single molecule samples 16 on a surface of the metal layer 14; and step (S13), detecting the single molecule samples 16 with a detector.

In step (S12), the disposing single molecule samples 16 includes the following sub-steps:

step (121): providing a single molecule sample solution;
step (122): immersing the carrier 10 into the single molecule sample solution; and
step (123): drawing the carrier 10 out of the single molecule sample solution.

In step (121), the molecular concentration of the single molecule sample solution can be in a range from about $10^{-7}$ mmol/L to about $10^{-12}$ mmol/L. In one embodiment, the molecular concentration of the single molecule sample solution is about $10^{-10}$ mmol/L.

In step (122), the carrier 10 is kept in the single molecule sample solution for a time from about 2 minutes to about 60 minutes so that the single molecule samples can be dispersed on the metal layer 14 uniformly. In one embodiment, the carrier 10 is kept in the single molecule sample solution for about 10 minutes.

In step (123), the carrier 10 is rinsed in water or ethanol for about 5 times to about 15 times and dried after being drawn out of the single molecule sample solution.

Figure 15:
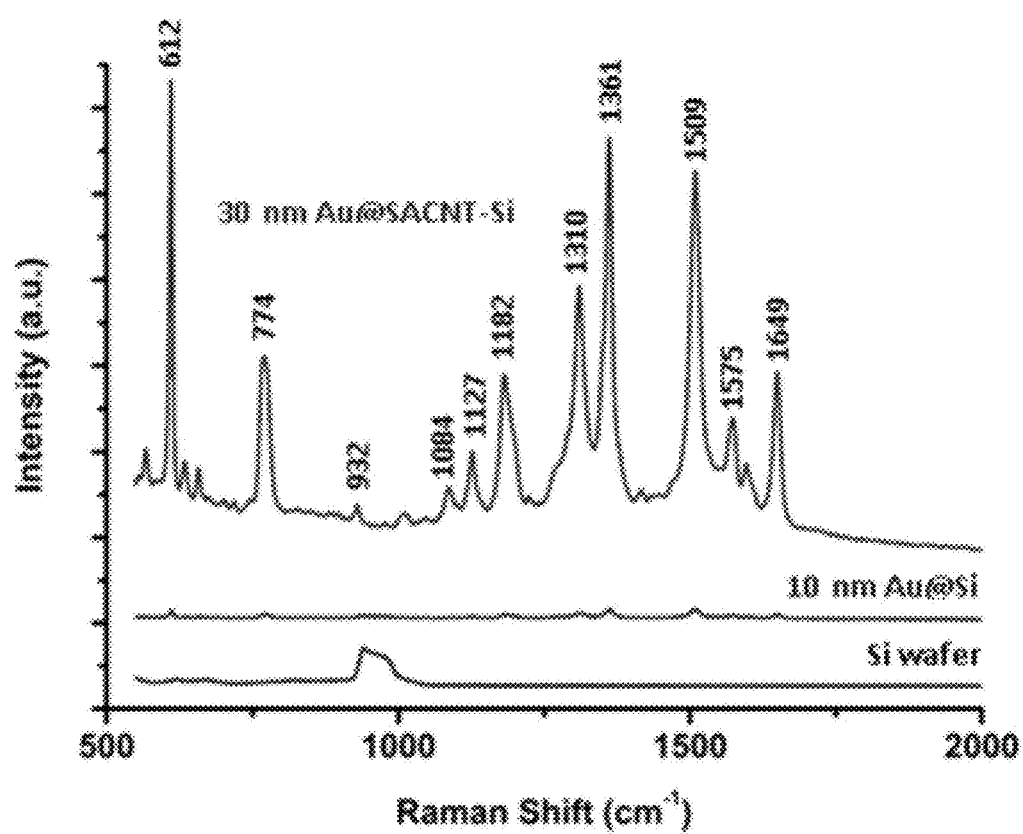
FIG. 15 is a Raman spectroscopy of Rhodamine molecules obtained by the method for detecting single molecules of FIG. 14.

In step (13), a Raman Spectroscopy system is used to detect the single molecule samples 16. In one embodiment, the Raman Spectroscopy system has an excitation source of He—Ne, an excitation wavelength of 633 nanometers, an excitation time of 10 seconds, a device power of 9.0 mW, and a working power of 9.0 mW×0.05×1. In one embodiment, Rhodamine single molecule samples 16 of $10^{-6}$ g/100 ml are disposed on the carrier 10 and radiated by the Raman Spectroscopy system for about 20 seconds. FIG. 15 shows a Raman spectroscopy of Rhodamine molecules using the carrier 10.

Figure 16:
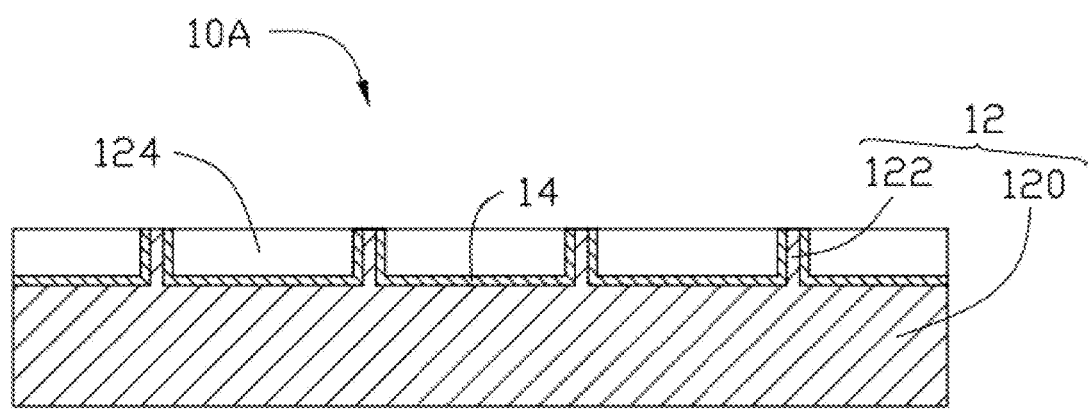
FIG. 16 is a schematic section view of another embodiment of a carrier for single molecule detection.

Referring to FIG. 16, a carrier 10A for single molecule detection of another embodiment is provided. The carrier 10A comprises a substrate 12 and a metal layer 14 located on the substrate 12. The substrate 12 comprises a base 120 and a patterned bulge 122 located on a surface of the base 120. The patterned bulge 122 comprises a plurality of strip-shaped bulges 125 intersected with each other to form a net and define a plurality of holes 124. The metal layer 14 is located on surfaces of the patterned bulge 122.

The carrier 10A is similar to the carrier 10 above except that the metal layer 14 is a discontinuous structure. The metal layer 14 is only located on side surfaces of the plurality of strip-shaped bulges 125 and bottom surfaces of the plurality of holes 124. The top surfaces of the plurality of strip-shaped bulges 125 are free of any metal layer. Alternatively, the metal layer 14 can be only located on bottom surfaces of the plurality of holes 124, and the top and side surfaces of the plurality of strip-shaped bulges 125 are free of any metal layer.

Figure 17:
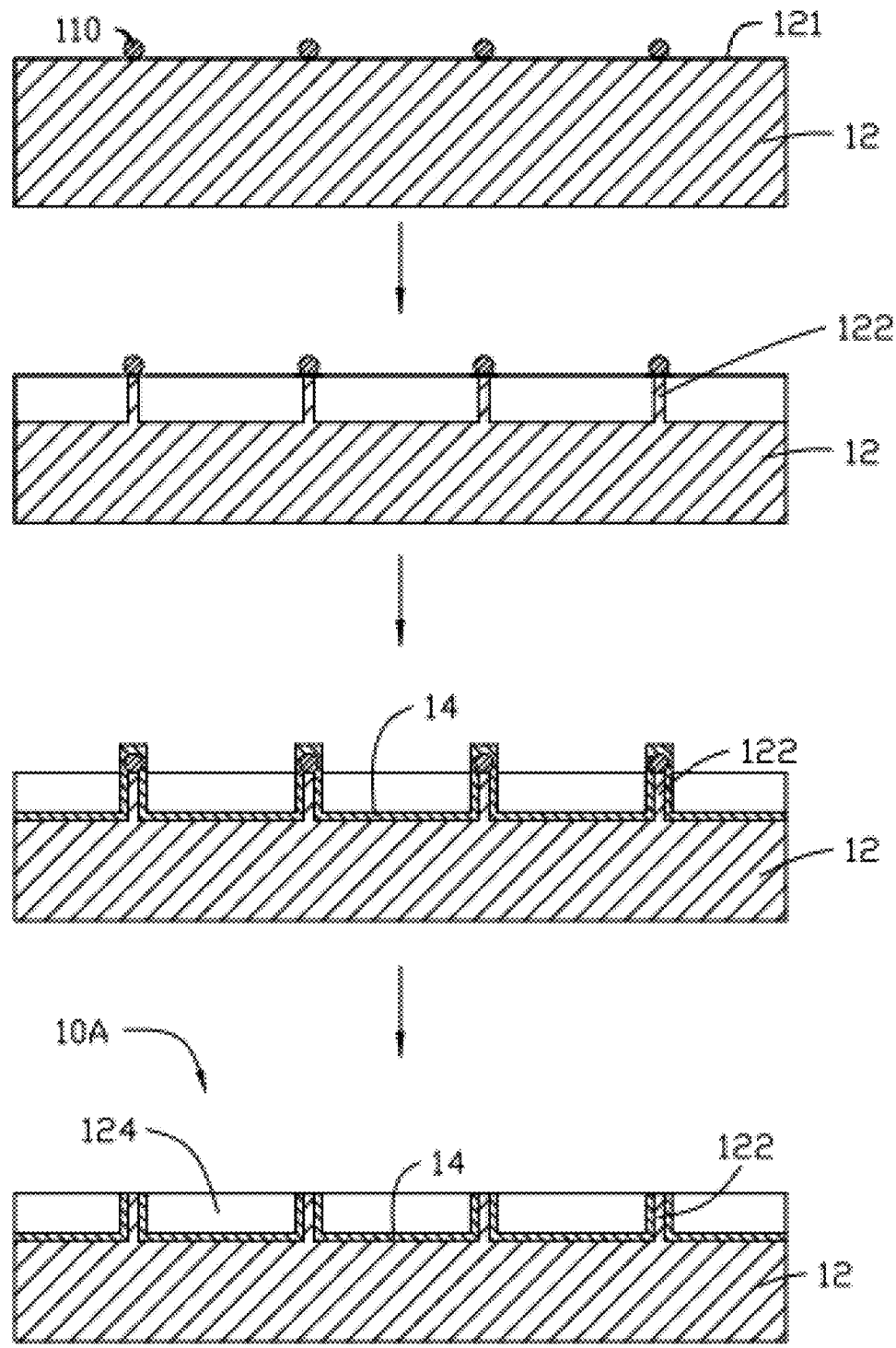
FIG. 17 is a flowchart of one embodiment of a method for making the carrier for single molecule detection of FIG. 16.

Referring to FIG. 17, a method for making the carrier 10A of one embodiment includes the following steps:

step (S10A), placing the carbon nanotube composite structure 110 on a surface 121 of the substrate 12, wherein parts of the surface 121 are exposed from the plurality of openings 116;

step (520A), forming the patterned bulge 122 on the surface 121 by dry etching the surface 121 using the carbon nanotube composite structure 110 as a first mask, wherein the patterned bulge 122 includes a plurality of strip-shaped bulges 125 intersected with each other;

step (S30A), applying the metal layer 14 on the patterned bulge 122 so that the metal layer 14 entirely covers both the patterned bulge 122 and the carbon nanotube composite structure 110; and step (S40A), removing the carbon nanotube composite structure 110.

The method for making the carrier 10A is similar to the method for making the carrier 10 above except the carbon nanotube composite structure 110 is removed after applying the metal layer 14 on the patterned bulge 122. In step (S30A), a first parts of the metal layer 14 are located on the surface of the carbon nanotube composite structure 110, and a second parts of the metal layer 14 are located on the side surfaces of the patterned bulge 122 and the bottom surfaces of the plurality of holes 124. In step (S40A), the first parts of the metal layer 14 are removed together with the carbon nanotube composite structure 110. Thus, a discontinuous metal layer 14 is obtained. The carbon nanotube composite structure 110 is used as a mask both for etching the surface 121 and depositing the metal layer 14. The cost is relatively lower and the efficiency is relatively higher. In one embodiment, the carrier 10A is also used to detect single molecule.

Figure 18:
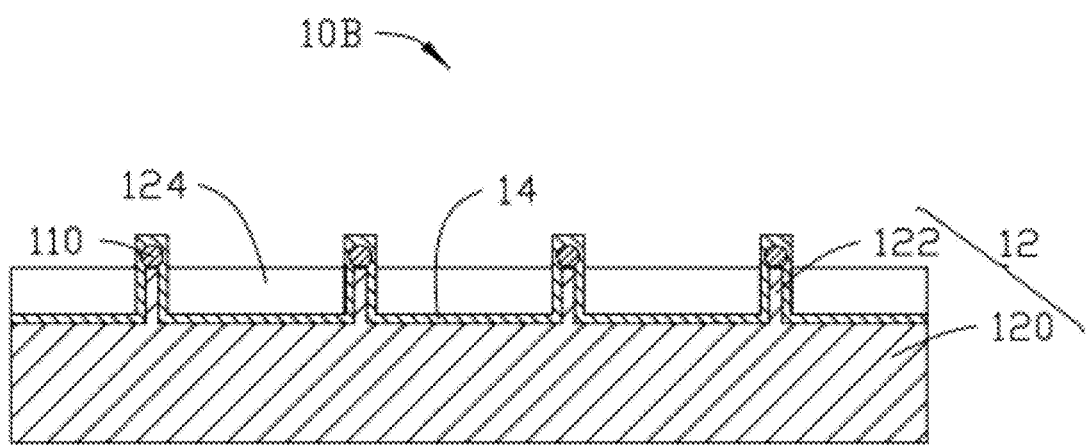
FIG. 18 is a schematic section view of another embodiment of a carrier for single molecule detection.

Referring to FIG. 18, a carrier 10B for single molecule detection of another embodiment is provided. The carrier 10B comprises a substrate 12 and a metal layer 14 located on the substrate 12. The substrate 12 comprises a base 120 and a patterned bulge 122 located on a surface of the base 120. The patterned bulge 122 comprises a plurality of strip-shaped bulges 125 intersected with each other to form a net and define a plurality of holes 124. The metal layer 14 is located on surfaces of the patterned bulge 122.

The carrier 10B is similar to the carrier 10 above except that the carrier 10B further comprises a carbon nanotube composite structure 110 located between the patterned bulge 122 and the metal layer 14. The metal layer 14 entirely covers both the patterned bulge 122 and the carbon nanotube composite structure 110. The carbon nanotube composite structure 110 is located the top surface of the plurality of strip-shaped bulges 125.

The method for making the carrier 10B is similar to the method for making the carrier 10A above except the step (S40A) is omitted. In one embodiment, the carrier 10B is also used to detect single molecule.

The carbon nanotube composite structure 110 and the patterned bulge 122 can form two layer of nano-scaled structure having the same pattern. The carbon nanotube composite structure 110 can further enhance the roughness of the top surfaces of the patterned bulge 122. Thus, the SERS of the carrier 10B will be further enhanced. Furthermore, the method for making the carrier 10B would have a relatively lower cost and relatively higher efficiency, and cause less pollution because the step (S40A) of removing the carbon nanotube composite structure 110 is omitted.

Figure 19:
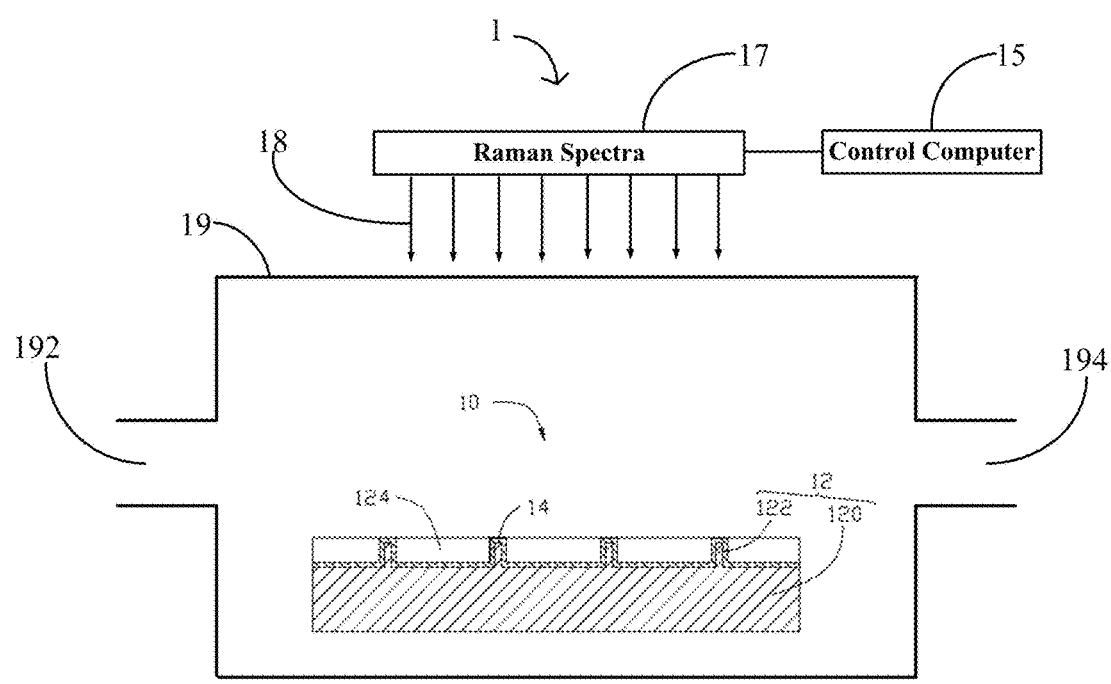
FIG. 19 is a schematic section view of another embodiment of a device for single molecule detection.

Referring to FIG. 19, a device 1 for single molecule detection of one embodiment is provided. The device 1 comprises a chamber 19, a carrier 10 located in the chamber 19, a detection device 17 located outside of the chamber 19, and a controlling computer 15 connected to the detection device 17.

The chamber 19 has an inputting hole 192 and an outputting hole 194. The chamber 19 includes a transparent window on the wall between the detection device 17 and the carrier 10. The patterned bulge 122 faces the detection device 17 so that the light emitted from the detection device 17 can reach the patterned bulge 122 of the carrier 10. In one embodiment, the detection device 17 is a Raman spectra.

In works, the liquid flows in to the chamber 19 from the inputting hole 192 and out of the chamber 19 from the outputting hole 194. Some of the liquid would be collected by the patterned bulge 122 and assembled on the metal layer 14. In one embodiment, the flow direction is substantially parallel to the substrate 12. The detection device 17 emit light to detect the liquid assembled on the metal layer 14, obtain a detection result, and send the detection result to the controlling computer 15. The controlling computer 15 receives and analyzes the detection result. Thus, the liquid flowed through the chamber 19 can be monitored in real-time.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A device for single molecule detection, the device comprising:
   a chamber having an inputting hole and an outputting hole;
   a carrier located in the chamber and comprising a substrate and a metal layer located on the substrate;
   a detection device located outside of the chamber; and
   a controlling computer located outside of the chamber and connected to the detection device;
   wherein the substrate comprises a base and a patterned bulge located on a surface of the base, the patterned bulge comprises a plurality of strip-shaped bulges intersected with each other to form a net and define a plurality of holes, and the metal layer is located on the patterned bulge.

2. The device of claim 1, wherein the plurality of strip-shaped bulges comprises a plurality of first strip-shaped bulges and a plurality of second strip-shaped bulges, the plurality of first strip-shaped bulges are substantially parallel with each other and extends along a first direction, and the plurality of second strip-shaped bulges are substantially parallel with each other and extends along a second direction different from the first direction.

3. The device of claim 2, wherein an angle between the first direction and the second direction is greater than 30 degrees and less than or equal to 90 degrees.

4. The device of claim 1, wherein each of the plurality of strip-shaped bulges has a width in a range from about 20 nanometers to about 150 nanometers and a height in a range from about 50 nanometers to about 1000 nanometers, and a distance between adjacent two of the plurality of strip-shaped bulges is in a range from about 10 nanometers to about 300 nanometers.

5. The device of claim 1, wherein each of the plurality of strip-shaped bulges has a width in a range from about 20 nanometers to about 50 nanometers and a height in a range from about 500 nanometers to about 1000 nanometers, and a distance between adjacent two of the plurality of strip-shaped bulges is in a range from about 10 nanometers to about 50 nanometers.

6. The device of claim 1, wherein the metal layer is a continuous structure.

7. The device of claim 6, wherein the metal layer covers entire surface of the patterned bulge.

8. The device of claim 1, wherein the metal layer is a discontinuous structure.

9. The device of claim 8, wherein the metal layer is located only on side surfaces of the plurality of strip-shaped bulges and bottom surfaces of the plurality of holes.

10. The device of claim 1, wherein a thickness of the metal layer is in a range from about 2 nanometers to about 200 nanometers.

11. The device of claim 1, wherein the metal layer comprises a material selected from the group consisting of gold, silver, copper, iron, nickel, and aluminum.

12. The device of claim 1, wherein the carrier further comprises a carbon nanotube composite structure located between the metal layer and the patterned bulge.

13. The device of claim 12, wherein the carbon nanotube composite structure is located on top surfaces of the patterned bulge.

14. The device of claim 12, wherein the carbon nanotube composite structure and the patterned bulge have the same pattern.

15. The device of claim 12, wherein the carbon nanotube composite structure comprises a carbon nanotube structure and a protective layer coated on the carbon nanotube structure, and the carbon nanotube structure comprises a plurality of carbon nanotubes intersected with each other.

16. The device of claim 15, wherein the protective layer comprises a material selected from the group consisting of metal, metal oxide, metal nitride, metal carbide, metal sulfide, silicon oxide, silicon nitride, and silicon carbide.

17. The device of claim 15, wherein the carbon nanotube structure comprises first carbon nanotube film and a second carbon nanotube film stacked with each other, the first carbon nanotube film comprises a plurality of first carbon nanotubes joined end to end and arranged along a third direction, and the second carbon nanotube film comprises a plurality of second carbon nanotubes joined end to end and arranged along a fourth direction different from the third direction.

18. The device of claim 1, wherein the detection device is a Raman Spectroscopy.

19. The device of claim 1, wherein the base and the patterned bulge are integrated, and the plurality of strip-shaped bulges are integrated.

20. The device of claim 19, wherein the base and the patterned bulge consist of a material selected from the group consisting of glass, quartz, silicon, silicon dioxide, silicon nitride, gallium nitride, gallium arsenide, alumina, and magnesia.

* * * * *